(12) United States Patent
Holwitt et al.

(10) Patent No.: US 8,790,877 B2
(45) Date of Patent: Jul. 29, 2014

(54) USING DNA APTAMERS AND QUANTUM DOTS FOR THE DETECTION OF PROTEINS OR OTHER TARGETS

(75) Inventors: Eric A. Holwitt, San Antonio, TX (US); Jonathan L. Kiel, Universal City, TX (US); Veronica Franz Sorola, San Antonio, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 265 days.

(21) Appl. No.: 12/217,833

(22) Filed: Jul. 9, 2008

(65) Prior Publication Data

US 2009/0053725 A1 Feb. 26, 2009

Related U.S. Application Data

(60) Provisional application No. 60/959,251, filed on Jul. 12, 2007.

(51) Int. Cl.
*C12Q 1/68* (2006.01)
*C07H 21/02* (2006.01)

(52) U.S. Cl.
USPC .......................................... 435/6.12; 536/22.1

(58) Field of Classification Search
USPC ..................................... 435/6; 536/22.1, 23.1
See application file for complete search history.

(56) References Cited

U.S. PATENT DOCUMENTS

| | | | |
|---|---|---|---|
| 5,928,862 A | 7/1999 | Morrison | |
| 6,500,622 B2 * | 12/2002 | Bruchez et al. | 435/6 |
| 6,569,630 B1 * | 5/2003 | Vivekananda et al. | 435/6.12 |
| 8,318,438 B2 | 11/2012 | Vivekananda et al. | |
| 2002/0045272 A1 | 4/2002 | McDevitt et al. | |
| 2004/0009514 A1 | 1/2004 | Frutos et al. | |
| 2004/0023265 A1 * | 2/2004 | Vivekananda et al. | 435/6 |
| 2005/0089864 A1 | 4/2005 | Li et al. | |
| 2005/0272088 A1 | 12/2005 | Cook et al. | |
| 2009/0004644 A1 | 1/2009 | Kiel et al. | |

OTHER PUBLICATIONS

Kiel, J.L. et al. Nanoparticle-labeled DNA capture elements for detection and identification of biological agents. In optically based biological and chemical sensing for defence (J.C. Carrano and A. Zukauskas ed.). Proceedings of SPIE 5617, pp. 383-387, 2004.*
Kiel, J.L. et al. DNA capture elements for rapid detection and identification of biological agents. In chemical and biological sensing V (P.J. Gardner, ed). Proceedings of SPIE 5416, pp. 105-110, 2004.*
Levy, M et al. Quantum-dot aptamer beacons for the detection of proteins. ChemBiochem, vol. 6, pp. 2163-2166, 2005.*
Holmberg et al., "The Biotin-Streptavidin Interaction Can Be Reversibly Broken Using Water at Elevated Temperatures," Electrophoresis. Feb. 2005;26(3):501-10. (Abstract only).

Lee et al., "Bioconjugates of CdTe Nanowires and Au Nanoparticles: Plasmon-Exciton Interactions, Luminescence Enhancement, and Collective Effects," Nano Lett., vol. 4, No. 12, 2323-2330, (2004) at p. 2324.
Pierce Protein Research Products catalog web page, "FITC and Fluorescein Dyes and Labeling Kits," available at: http://www.piercenet.com/browse.cfm?fldID=B3D952BB-8404-460C-B6F3-410E23D78308.
Weber et al., "Structural Origins of High-Affinity Biotin Binding to Streptavidin," Science Jan. 6, 1989: vol. 243 No. 4887 pp. 85-88, at p. 85.
Kiel, J.L., et al. "Nanoparticle—labeled DNA Capture Elements for Detection and Identification of Biological Agents." In Optically Based Biological and Chemical Sensing for Defence (J.C. Carrano and A. Zukauskas, eds.), Proceedings of SPIE 5617: 382-387; (2004).
Kiel, J.L., et al., "Specific biological Agent Taggants." In Chemical and Biological Sensing VI (P.J. Gardner, ed.), Proceedings of SPIE 5795: 39-45; (2005).
Kiel, J.L., et al., "DNA Capture Elements for Rapid Detection and Identification of Biological Agents." In Chemical and Biological Sensing V (P.J. Gardner, ed.) , Proceedings of SPIE 5416:105-110; (2004).
Levy, M., et al., "Quantum-Dot Aptamer Beacons for the Detection of Proteins." ChemBioChem 2005; 6:2163-2166.
Service, R.F., "Color-Changing Nanoparticles Offer a Golden Ruler for Molecules." Science, 308:1099; (May 20, 2005).
Giepmans, Ben N.G., et al., "The Fluorescent Toolbox for Assessing Protein Location and Function." Science, 312: 217-224; (Apr. 14, 2006).
Moerner, W.E. and Orrit, Michel, "Illuminating Single Molecules in Condensed Matter.", Science, 283: 1670-1676; (Mar. 12, 1999).
Michalet, X., et al., "Quantum Dots for Live Cells, in Vivo Imaging, and Diagnostics.", Science, 307: 538-544; (Jan. 28, 2005).
Howlitt and Franz, "A Quantum Dot DNA Aptamer Linked System for Detecting Proteins", Abstract No. MEDI 539, for Poster Sessions at the 232nd American Chemical Society National Meeting, San Francisco, CA., Sep. 10-14, available at 2006http://oasys2.confex.com/acs/232nm/techprogram/P1011036.HTM (Note: Abstracts were publicly available on Jul. 17, 2006).
Kiel, Johnathan L., et al., ELISA-Like Format for Comparing DNA Capture Elements (Aptamers) to Antibody in Diagnostics Efficacy, 2004 Scientific Conference on Chemical & Biological defense Research Nov. 15-18, 2004, Hunt Valley, Maryland.

(Continued)

*Primary Examiner* — Prabha Chunduru
(74) *Attorney, Agent, or Firm* — AFMCLO/JAZ; Rebecca Greendyke; Paul Heydon

(57) ABSTRACT

The solutions provided here use DNA aptamers and quantum dots for the detection of bacteria, viruses, proteins or other targets. An example of a method described here comprises: providing a complex of DNA complementary strands, one strand being an aptamer, having one strand covalently linked to a quantum dot, and having the other strand linked to a quencher; and contacting the complex of DNA complementary strands with a microorganism or components thereof, under conditions that permit binding of the aptamer with the microorganism or components thereof.

10 Claims, 4 Drawing Sheets

(56) References Cited

OTHER PUBLICATIONS

Thirumalapura, Nagaraja Ramavadhani, "Application of Molecular Methods in Diagnostics of Bacterial Pathogens," Submitted to the Faculty of the Graduate College of the Oklahoma State University in partial fulfillment of the requirements for the Degree of Doctor of Philosophy. May 2005.

Baldrich, Eva, et al.. "Displacement Enzyme Linked Aptamer Assay," Anal. Chem. 2005, 77(15),4774-4784.

Drolet, D.W., et al., An enzyme-linked oligonucleotide assay. Nat Biotechnol 1996;8:1021-1025.

Grunow R, et al., Detection of *Francisella tularensis* in biological specimens using a capture enzyme-linked immunosorbent assay, an immunochromatographic handheld assay, and PCR. Clin Diag Lab Immunol Jan. 2000; 7 (1):86-90.

Menini, Stefano, et al., "Inside Lab Invest, Aptamer-linked immobilized sorbent assay: the next ELISA?", Laboratory Investigation (2006) 86, 535-537.

Lee, M., et al., "A fiber-optic microarray biosensor using aptamers as receptors," Analytical Biochemistry 282, 142-146 (2000).

Liss, M., et al., "An aptamer-based quartz-crystal protein biosensor," Analytical Biochemistry, 2002, 74: 4488-4495.

Porsch-Ozcurumez, M., et al., Comparison of enzyme-linked immunosorbent assay, western blotting, microagglutination, indirect immunofluorescence assay, and flow cytometry for serological diagnosis of tularemia. Clin Vaccine Immunol Nov. 2004, vol. 11, No. 6:1008-1015.

Rye, P.D., et al., "Immunomagnetic DNA aptamer assay," BioTechniques 30:290-295 (Feb. 2001).

Vivekananda, J., et al., "Anti-*Francisella tularensis* DNA Aptamers Detect Tularemia Antigen From Different Subspecies by Aptamer-Linked Immobilized Sorbent Assay," Laboratory Investigation (2006) 86, 610-618 (published online Mar. 20, 2006).

Yang, X., et al., "Immunofluorescence assay and flow-cytometry selection of bead-bound aptamers," Nucleic Acids Res, 2003, vol. 31, No. 10 e54.

Frutos, A.G., et al., "Method for detection of single-base mismatches using bimolecular beacons," J Am Chem Soc 124(11): 2396-2397 (2002).

Dyadyusha, D., et al., "Quenching of CdSe quantum dot emission, a new approach for biosensing," Chem Commun:3201-3203 (2005).

Zhu, H., et al., "Aptamer based microsphere biosensor for thrombin detection," Sensors 6:785-95, Aug. 16, 2006.

Fan, M., et al., "Aptamer selection express: A novel method for rapid single-step selection and sensing of aptamers," Journal of Biomolecular Techniques 19:311-321 (2008).

Gill, R., et al., "Fluorescence resonance energy transfer in CdSe/ZnS-DNA conjugates: probing hybridization and DNA cleavage," J. Phys. Chem. B 109:23715-9, published online Nov. 19, 2005.

* cited by examiner

FIG. 3

STX= Shiga toxin; OV= ovalbumin

FIG. 4
Black = Shiga
Gray = Ovalbumin control

De-Quenching Quantum Dot/Shiga Toxin Aptamers in a Microtiter Plate Format with Immobilized Toxin Compared to Ovalbumin Immobilized Controls

Quantum Dot Volume (microliters)

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic Oligonucleotide

<400> SEQUENCE: 1
ggtaactagc attcatttcc cacacccgtc ccgtccatat                          40

<210> SEQ ID NO 2
<211> LENGTH: 19
<212> TYPE: DNA
<213> ORGANISM: Artificial Sequence
<220> FEATURE:
```

```
<221> NAME/KEY: misc_feature
<222> LOCATION: (1)..(19)
<223> OTHER INFORMATION: Synthetic Oligonucleotide

<400> SEQUENCE: 2
atatggacgg gacgggtgt                                                    19
```

USING DNA APTAMERS AND QUANTUM DOTS FOR THE DETECTION OF PROTEINS OR OTHER TARGETS

RELATED APPLICATIONS, AND RIGHTS OF THE GOVERNMENT

This application claims the benefit under 35 U.S.C. §119(e) of provisional Patent Application Ser. No. 60/959,251, filed on Jul. 12, 2007, the entire text of which is incorporated herein by reference. This application is related to U.S. patent application Ser. No. 11/965,039, entitled Methods and Compositions for Processes of Rapid Selection and Production of Nucleic Acid Aptamers, filed by Kiel et al. on Dec. 27, 2007 (the entire text of which is incorporated herein by reference) which claims the benefit under 35 U.S.C. §119(e) of provisional Patent Application No. 60/882,454, filed on Dec. 28, 2006. This application is related to U.S. patent application Ser. No. 12/072,758, entitled Aptamer-Based Assays, filed by Jeevalatha Vivekananda and Johnathan L. Kiel on Feb. 27, 2008 (the entire text of which is incorporated herein by reference), which claims the benefit under 35 U.S.C. §119(e) of provisional Patent Application Ser. No. 60/904,900, filed on Mar. 1, 2007.

RIGHTS OF THE GOVERNMENT

The invention described herein may be manufactured and used by or for the Government of the United States for all governmental purposes without the payment of any royalty.

BACKGROUND OF THE INVENTION

The invention relates to assays and more particularly to testing biological samples.

Conventional immunoassays usually are of the sandwich/capture assay type requiring a capture antibody or anti-ligand and an identification antibody with either an enzyme or a fluorescent tag indicating presence of the ligand of interest.

What is needed is a test that requires fewer steps and less time to conduct.

SUMMARY OF THE INVENTION

The solutions provided here use DNA aptamers and quantum dots for the detection of bacteria, viruses, proteins, or other targets. An example of a method described here comprises: providing a complex of DNA complementary strands, one strand being an aptamer, having one strand covalently linked to a quantum dot, and having the other strand linked to a quencher; and contacting said complex of DNA complementary strands with a microorganism or components thereof, under conditions that permit binding of said aptamer with said microorganism or components thereof. In some examples described here, the methods and systems are extremely simple to use and appear to have several advantages over the traditional ELISA. Since no blocking steps are required and the number of washing steps is reduced, the time required to conduct the test is greatly reduced. In some examples described here, a quantum dot aptamer complex comprises one strand of a duplex DNA molecule linked to the quantum dot by an amide bond. It does not matter if the aptamer or the complementary strand is attached. However, the strand that is not attached contains a non-radiative quencher. Upon addition of the aptamers' target, the amount of light emitted by the quantum dots increases. In some examples described here, the methods and systems can also be used in reverse, with the aptamers' target immobilized on a microliter plate. This permits an assay like a competitive immunoassay.

BRIEF DESCRIPTION OF THE DRAWINGS

FIG. 3 is a graph providing data concerning Example 1.
FIG. 4 is a graph providing data concerning Example 2.

DETAILED DESCRIPTION

We describe examples using aptamers for capturing and reporting the presence of a target, such as a pathogen. Aptamers are single-stranded oligonucleotides with a length of tens of nucleotides, exhibiting high affinity and specificity towards any given target molecule. Aptamers have highly defined tertiary structures, which allow them to form stable and specific complexes with a range of different targets, including amino acids, proteins and whole viruses. In contrast with a conventional immunoassay, the example assays described here use DNA aptamers instead of antibodies in an immunoassay-like procedure. The example assays described here do not require the formation of a sandwich, and binding of the ligand of interest causes an increase in signal from the fluorescent marker.

Figure 1:
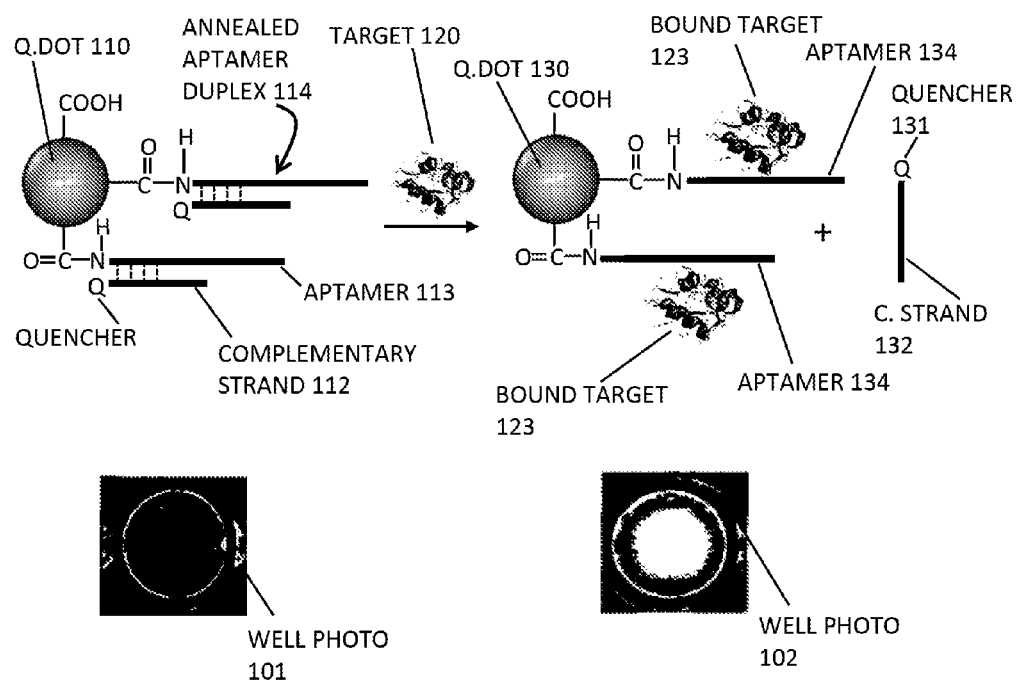
FIG. 1 is a simplified diagram showing an example of DNA aptamers linked to quantum dots, quenching, and dequenching.

Referring first to FIG. 1, this example comprises a complex of DNA complementary strands (duplex 114) covalently linked to a fluorescent nanocrystal (quantum dot 110), and a fluorescent quencher 111. Optionally, a magnetic particle (not shown) may be included in the complex 114. The nanocrystal (quantum dot 110) and quencher 111 are on separate DNA strands. In FIG. 1, one strand (aptamer 113) of a duplex DNA molecule is linked to the quantum dot 110 by an amide bond. It does not matter if the aptamer 113 or the complementary strand 112 is attached to quantum dot 110. However, the strand that is not attached (complementary strand 112 in FIG. 1) contains a non-radiative quencher 111. Black Hole Quencher 2® (BHQ2) was the quencher used in examples described below, but other kinds may be used. Upon addition of the aptamers' target 120, aptamer 134 and complementary strand 132 are separated by binding of the target (bound target 123) to aptamer 134. Quencher 131 on complementary strand 132 is separated from quantum dot 130. The nanocrystal fluorescence is de-quenched and observable by eye or by a fluorescent reader (fluorometer). The amount of light emitted by the quantum dot 130 increases (compare well photo 101 and well photo 102).

Another example described below (see left side of FIG. 2) comprises a complex of DNA complementary strands (duplex 214) covalently linked to fluorescent nanocrystal (quantum dot 210), and a fluorescent quencher 211, all attached to the bottom of the well 201 of a microtiter plate. In an alternative format, a magnetic particle (micron-sized or a nanoparticle, not shown) is also used to attach the complex to the bottom of the wells of the plate by a magnet placed under the plate. The quantum dot 210 and quencher 211 are on separate DNA strands, complementary strand 232 and aptamer 213. When these are separated by binding of a target 220, which the aptamer 213 is made specifically to bind, the nanocrystal fluorescence is de-quenched and observable by a fluorescent reader (microtiter plate reading fluorometer). In an alternative format, a magnetic particle (not shown) facilitates the separation of the two strands by magnetic capture of one of them, being attached only to one of them either covalently by conjugation chemistry or by a DNA positive and negative strand complementation different from that of the aptamer double strand being separated. This complementation of the magnetic particle DNA may be made covalent by chemically cross-linking the two complementary strands. The de-quenched complex is either magnetically or covalently immobilized on the bottom of the wells of the microliter plate so that the supernatant can be removed or washed away containing the freed quencher strand of DNA.

The method and system can also be used in reverse (see the right side of FIG. 2) with the aptamers' target 221 immobilized on a microtiter plate well 202. Aptamer 214 and complementary strand 233 are separated by binding of the target to aptamer 214. Quencher 212 on complementary strand 233 is separated from quantum dot 211.

Figure 2:
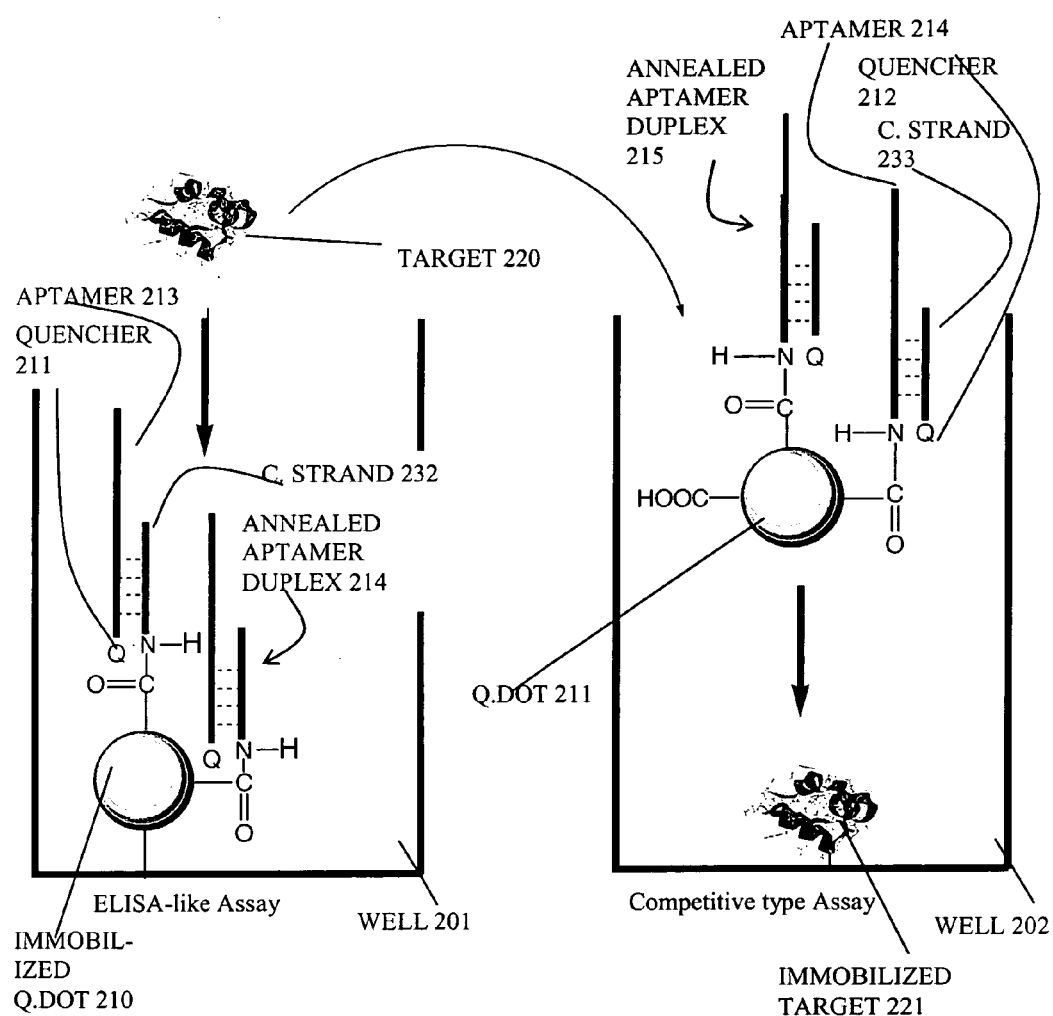
FIG. 2 is a simplified diagram showing examples of assays.

FIG. 1 and FIG. 2 are simplified diagrams showing examples with two aptamers per quantum dot. However, the invention is not so limited. Example 2 described below has an 8:1 ratio of aptamers to quantum dots, and other ratios may be used.

EXAMPLE 1

Preparation of a Reactive Plate

A maleic anhydride plate (Pierce Biotechnologies) was reacted with an amino dPEG24 acid (polyethylene glycol linker) to provide a tether to the surface of the plate. This plate was allowed to react overnight in carbonate buffer on the Jitterbug plate shaker. The contents of each well were discarded and washed twice with 200 µl of PBS pH 7.0 buffer, then once with 200 µl of methanol. Next, the carboxylic acid end of this tether was then reacted with NHS (N-hydroxy succinimide) and EDC (1-ethyl-3-[3-dimethylaminopropyl] carbodiimide hydrochloride) to couple NHS to the carboxylic group and set it up for reaction with a primary amine. The reaction was carried out in methanol. The plate was washed twice with methanol and resuspended in methanol. The plate was covered in parafilm and stored in the fridge.

Preparation of Annealed Aptamer Complex

The aptamer strand of approximately 40 nucleotides was annealed to its complement, which was approximately 21 nucleotides. Either the aptamer contained a 5' amine and the complementary strand a 3' quencher or the aptamer contained a 3' quencher and the complementary strand a 5' amine. Further a 3' amine could be used with a 5' quencher. The strands were annealed in 10 mM NaCl, 0.1M MOPS buffer, pH 7.0 by heating to 85° C. for fifteen minutes in a water bath and while still in the water bath cooled to room temperature. Strands were stored refrigerated.

Quenching of Quantum Dots and Immobilization onto Plate

The annealed strands were conjugated to T1 or T2 Carboxyl Birch Yellow quantum dots. These dots and strands were mixed with a molar ratio of approximately 8 duplex DNA strands per dot. The reaction was carried out in 0.1M MOPS, pH 7.0 buffer supplemented to a concentration of 10 mM NaCl. 5 mg of EDC was dissolved in 5 ml of MOPS buffer, and 1 ml added to the reaction. This was repeated three to five times (usually a total of 5 mg of EDC was added). The dots were allowed to react overnight and EDA (~16 mg) was added in the morning along with additional amounts of EDC (~3 mg) to couple the EDA. The dots were filtered (Amicon® Ultra Spin filters, 100,000 NMCO) and washed with PBS and Tween 20 (0.025%). The dots were washed enough to remove all the unreacted EDA. These dots were then added (50 µl) to a plate with NHS activated carboxyl groups via the amino dPEG24 acid-tether. The plate was allowed to shake for three hours and then left to stand overnight without shaking. The next morning the wells were washed with three times with 200 µl PBS.

Plate Assay

Shiga Toxin, purchased as a lyophilized powder in PBS, was reconstituted to two milliliters using deionized water. This brought the concentration of toxin to 0.25 mg/ml.

Ovalbumin, purchased from Sigma-Aldrich® was also reconstituted in deionized water to bring the final concentration to 1.0 mg/ml. Increasing milliliter quantities of both Shiga toxin and ovalbumin were added in triplicates to wells containing immobilized dots. These microliter quantities ranged from three up to one hundred. The total volume of the wells was brought to 100 µl using PBS. The plate was allowed to shake on the Jitterbug plate shaker for one hour, starting at 25° C. and ramping up to 37° C. The contents of each well were discarded and washed twice with 200 µl PBS. The wells were then reconstituted in 100 µl PBS and read using the Synergy Plate Reader.

Figure 3:
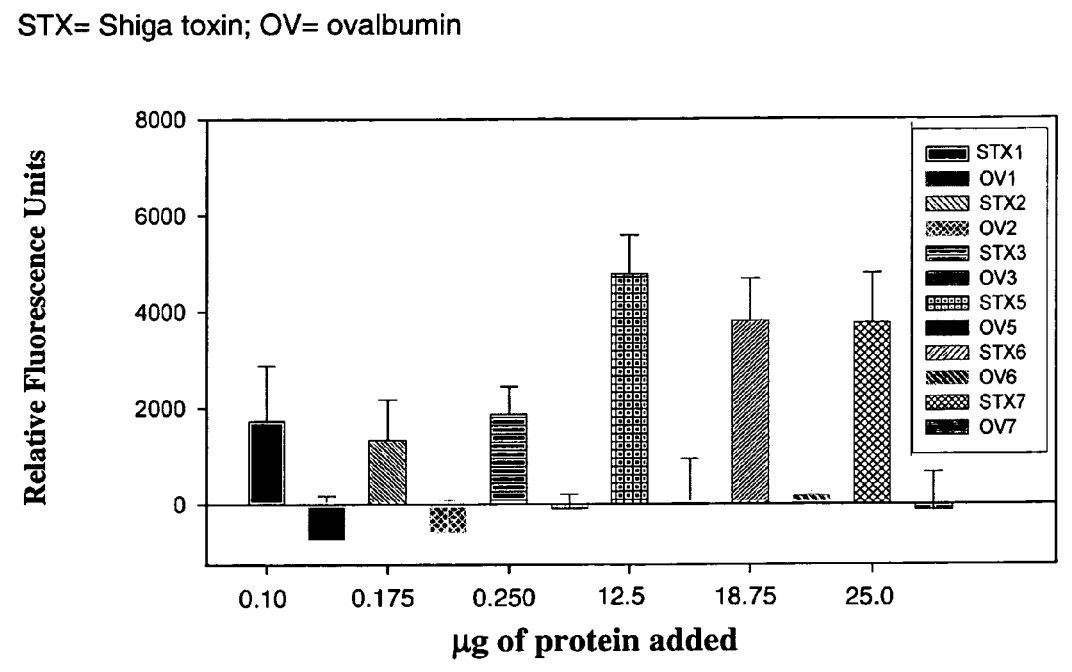

For results, see FIG. 3. The control wells to which ovalbumin was added showed no increase in fluorescence across the entire range of the experiment. However, while the increase in fluorescence of the immobilized aptamer-quantum dot complex was not linear, every well to which shiga toxin was added showed an increase in fluorescence across the entire range of the experiment (0.10 µg to 25 µg of shiga toxin added).

The indirect assay measures the interference with the baseline de-quenched fluorescence of adding free complex to the bound control agent. It can measure antibody in the sera of a patient against the agent (when isolating the agent is not practicable) or can be used to measure interference with bound de-quenched fluorescence of the complex when soluble antigen activates quenched complexes that are removed with the supernatant wash out.

This example does not require extensive washing (at most a one step separation of the freed quencher strand from the covalently bound complex or the magnetically bound complex) and does not require separate capture and reporter anti-ligands. It is not a typical sandwich assay in which a separate capture anti-ligand (like antibody) and a separate reporter anti-ligand (like fluorescent antibody or enzyme-linked antibody) must be added in separate steps with their accompanying washing steps.

Finally, some variations to this example are possible. Although the bound complex added to the microtiter plates may be read in situ for agent or by interference for antibody or competition with control bound agent, it can also be transferred by the release of the magnetically captured agent for further analysis by orthogonal methods such as PCR performed on the DNA from the magnetically captured agent or cultured directly off these complexes.

EXAMPLE 2

Annealing the Aptamer

Plus ST J-9 was an anti-shiga toxin aptamer, disclosed as "SEQ ID NO:8" by Jeevalatha Vivekananda and Johnathan L. Kiel, in United States Patent Application 20040023265 A 1, Methods And Compositions For Nucleic Acid Ligands Against Shiga Toxin And/Or Shiga-Like Toxin, Feb. 5, 2004 (the entire text of which is incorporated herein by reference). The aptamer was modified with a 3' amine for attachment to a quantum dot. Negative ST J-9 was an oligonucleotide strand complementary to the 3' end of ST J-9, the anti-shiga toxin aptamer. At its 5' end it had a Black Hole Quencher (BHQ2) to quench the quantum dot. Oligonucleotides were purchased from Biosearch Technologies®, Inc.

Plate Assay

Shiga Toxin was coupled to Reacti-Bind Maleic Anhydride Plates (Pierce Biotechnologies). Lyophilized shiga toxin powder (Toxin Technologies) was reconstituted in 2 ml of Dl water. Ovalbumin (Sigma Aldrich) was reconstituted in Dl water to give a molar concentration similar to that of shiga toxin. A carbonate buffer of pH 9.2 was prepared.

```
SEQ ID NO:1. Plus STJ-9:
5' G GTA ACT AGC ATT CAT TTC CCA CAC CCG TCC CGT CCA TAT 3'

SEQ ID NO:2. Negative STJ-9:
5' ATA TGG ACG GGA CGG GTG T 5'BHQ2
```

The number of moles of the two strands were compared. The strand with the largest number of nanomoles was dissolved in 1 ml of 0.1M MOPS (3-(N-morpholino) propanesulfonic acid), 10 mM NaCl, pH 7.2 and a volume transferred to the other oligonucleotide such that the Negative STJ-9 strand would be in excess. This was to assure complete annealing of the amino labeled positive strand, to have no unannealed Plus STJ-9 present after the annealing step. The oligonuleotides were annealed (wrapped in aluminum foil to prevent bleaching of the quencher (BHQ2)) with stirring at 75 to 80° C. for 15 minutes. The solution was cooled in the water bath to room temperature before refrigeration.

Preparation of Positive Control

Plus ST J-9 was dissolved in 1 ml of MOPS buffer. A volume of plus ST J-9 was mixed with carboxyl functionalized Birch Yellow T1 Evitags® (Evident Technologies, Inc.) such that the ratio of oligonucleotide to Evitag was 4:1. EDC (1-ethyl-3-[3-dimethylaminopropyl]carbodiimide hydrochloride) dissolved in MOPS buffer was added to the mixture using the following steps: dissolve 5 mg EDC in 5 ml of 0.1M MOPS, pH 7.2, add 1 ml to the reaction, and shake on a rotary stirrer at room temperature. This was repeated approximately every 15 to 20 minutes for a total of five additions, after which the reaction was allowed to proceed at room temperature for another 2 hours. To isolate the Evitags from the reactants and products, an Amicon Ultra Centrifugal Spin Filter was used with a molecular weight cutoff of 100,000 Daltons. The Evitags were washed once with 0.05% Tween 20 in PBS and several times with PBS and concentrated to their initial volume before refrigeration.

Preparing the Quenched Quantum Dots

The annealed oligonucleotide was mixed with carboxyl functionalized Birch Yellow T1 Evitags at a ratio of oligonucleotied to Evitag of approximately 7:1. EDC (1-ethyl-3-93-dimethylaminopropyl carbodiimide hydrochloride) dissolved in MOPS buffer was added to the mixture: dissolve 5 mg EDC in 5 ml of MOPS and add 1 ml to the reaction and shake on a rotary stirrer at room temperature. This was repeated approximately every 15 to 20 minutes for a total of five additions, after which the reaction was allowed to proceed at room temperature for another 2 hours. To isolate the Evitags from the reactants and by-products, an Amicon Ultra Centrifugal Spin Filter was used with a molecular weight cut off of 100,000 Daltons. The Evitags were washed several times with PBS and concentrated to their initial volume before refrigeration.

To each well of a 96-well Reacti-Bind Maleic Anhydride Plates (Pierce Biotechnologies) was added 50 μl of either shiga toxin or ovalbumin and 50 μl of bicarbonate buffer. Both proteins were allowed to react with the plate for two hours at room temperature. The contents of each well were discarded, and the washed twice with PBS, pH 7.4. Quenched Birch Yellow quantum dots were then added to wells and allowed to react at 37o C for thirty minutes and at room temperature for thirty minutes with shaking. The wells were then washed three times with 200 μl aliquots of PBS and reconstituted in 100 μl of PBS. The wells were then read by a Synergy Plate reader system.

For results, see FIG. 4. The data is reported in relative fluorescence units. Either Shiga toxin or ovalbumin were immobilized on Pierce Reacti-bind plates. Fifty pi of protein solution were added to the wells (shiga toxin concentration 0.25 mg/ml, total protein 1.0 mg/ml, ovalbumin 0.5 mg/ml). The number of reactive sites per well was 110 picomoles. The maximum amount of shiga toxin in a well was approximately 3 micrograms (5×10−11 mols). To each well was added the indicated volume of the aptamer-quantum dot complex (concentration of quantum dots is 4.5 nanomoles/ml; 25 μl=0.112 nanomoles of quantum dots; ratio of aptamer:quantum dots=8:1. As the volume of aptamer-quantum dot complex increased, the fluorescence showed a linear increase from the wells with shiga toxin, indicating the aptamer-quantum dot complex was binding to the toxin and dequenching. The control, ovalbumin, shows no such increase in fluorescence, indicating that the aptamer-quantum dot complex was not binding either specifically or non-specifically to the ovalbumin or the well.

FITC Labeled Anti-Shiga Toxin Antibody

For a comparison of quantum dot/aptamer complex (not quenched) with fluorescently labeled antibody against shiga toxin and ovalbumin, shiga toxin and ovalbumin were immobilized on Pierce Reacti-bind plates and either qdot/aptamer complex or antibody was added. The data (not shown here) demonstrated that the aptamer behaved similarly to the antibody. FITC labeled anti-shiga toxin antibody was purchased from Toxin Technologies to verify that shiga toxin was bound to the Reacti-Bind Maleic Anhydride Plates. For binding reactions with the antibody and positive control, the wells were first blocked with a blocking solution made of 3% dry milk in tris-buffered saline, pH 7.5. After 1 hour at 37 C, the wells were washed twice with PBS, and either antibody or positive control added and incubated as described for the quenched Evitags. Afterwards the wells were washed 3 times with PBS and reconstituted in 100 ul of PBS. The fluorescence was measured using a Synergy Plate Reader.

This example does not require extensive washing (at most a one step separation of the freed quencher or complementary metallic nanoparticle strand from the magnetic capture nanoparticle strand) and does not require separate capture and reporter anti-ligands. It is not a typical sandwich assay in which a separate capture anti-ligand (like antibody) and a separate reporter anti-ligand (like fluorescent antibody or enzyme-linked antibody) must be added in separate steps with their accompanying washing steps.

Finally, some variations to this Example 2 are possible. Another version uses two different types of metallic nanoparticles, one magnetic the other not with different metallic compositions. The nanoparticles of different metallic composition are chemically linked to the aptamer and complementary strands, respectively. They are read by elemental analysis of their light emission spectra using laser induced breakdown spectroscopy. When the two strands are joined, the spectrum contains a given proportion of the spectral lines of the elemental composition of both nanoparticles. When the magnetic one is magnetically trapped and the other is separated by binding of the ligand or chemical or physical interaction, then the laser induced breakdown spectroscopy shows a loss of the other particle's metallic elemental spectral lines.

Some variations may detect and identify bioterrorism or biowarfare agent contamination of the surfaces of military equipment (including the interior of aircraft) and personnel. Some variations may determine the viability of such agent on such a surface by measuring the binding of aptamers to surface ligands of biological agents associated with toxic activity, infectivity, or pathogenicity by the de-quenching or metallic nanoparticle separation method. This use extends to the action of enzymes such as DNAase, phospholipase or lipase or protease or the cleavage of some other chemical linkage that could remove the binding of fluorescent quencher from the nanocrystal surface by a chemical (acid or base interaction) or physical action (i.e. detergent that dissolves a lipid coating on the nanocrystal releasing the quencher or by heating the particle to release it) that may or may be not directly associated with the melting of the DNA capture element double strand. In some instances, it would be associated with its cleavage, including modified DNA (addition of peptides or other chemical groups susceptible to such cleavage) or physical release. Some variations may involve nanoparticle LIBS (laser induced breakdown spectroscopy) tagging and separation. This assay can also be used with pre-labeled particles (tagged biological material) that when collected in a release (i.e. aerosol collected in an impinger, cyclone, or on a filter) the nanoparticles can be collected and read with LIBS such that the spectral complementation of the particles is present (that is, still linked by the DNA complementation or by binding to the target biological particles) or separated or lost (because of destruction of the biological agent linker or the DNA complementation). Some variations are suitable for testing decontamination methods and release of biological agents (for instance, in an air ventilation system of a building) and for measuring destruction of the released agent (loss of complementation). This can even be done on the fly by using spark induced breakdown spectroscopy (passing the aerosol through a spark gap and looking at the spectrum of the light emission from the spark). Some variations may involve labeling of bacterial spores with separate or combined rare earth metals. The linkage of the nanoparticle to the biological agent may be directly from the metallic nanoparticle or by plasmid DNA containing aptamer/diazoluminomelanin couplets that chelate the rare earth metals specifically to the biological target.

Although the complex added to the surface may be read in situ for agent, it can also be collected and further analyzed with greater sensitivity in a fluorometer or with a LIBS or SIBS device (the latter referring to the metallic nanoparticle only version). Also, the components: DNA, nanocrystals, in some cases diazoluminomelanin (DALM), and metallic nanoparticles require no refrigeration, can be kept in the dry state until used, and are much more stable than fluorescent organic compounds and antibody or other peptide-based anti-ligands and require a single excitation (the nanocrystals and DALM) wavelength (360 nm to 395 nm) to achieve a broad range of emissions (400 nm to 800 nm), or no excitation wavelength at all oust an electrical discharge—i.e. the LIBS or SIBS for metallic nanoparticles or the DALM/chelated metal complexes). They also afford magnetic collection for further analysis by other orthogonal methods.

In summary, examples provided here use DNA aptamers and quantum dots for the detection of bacteria, viruses, proteins or other targets. The examples provided herein are intended to demonstrate only some embodiments of the invention. Other embodiments may be utilized and structural changes may be made, without departing from the present invention.

We claim:

1. A method comprising:
    providing a complex of DNA complementary strands, one strand being an aptamer comprising SEQ ID NO: 1, wherein said strand is covalently linked to a quantum dot and the other strand is linked to a quencher; and
    contacting said complex of DNA complementary strands with a microorganism or components thereof under conditions that permit binding of said aptamer with said microorganism or components thereof.

2. The method of claim 1, wherein said complex of DNA complementary strands further comprises at least one metallic particle.

3. The method of claim 2, further comprising separating said complex of DNA complementary strands by magnetic capture of one strand, wherein said at least one metallic particle is magnetic.

4. The method of claim 1, further comprising immobilizing said complex of DNA complementary strands on a microtiter plate.

5. The method of claim 1, further comprising immobilizing said aptamer's target on a microtiter plate.

6. The method of claim 1, further comprising detecting whether said aptamer's target is present on an object's surface.

7. A method comprising:
    providing a complex of DNA complementary strands, one strand being an aptamer comprising SEQ ID NO: 1, wherein said strand is covalently linked to a quantum dot and the other strand is linked to a quencher;
    contacting said complex of DNA complementary strands with a sample; and
    detecting whether said aptamer's target is present in the sample.

8. The method of claim 7, wherein said contacting further comprises adding said sample to a microtiter plate pre-coated with said complex of DNA complementary strands.

9. The method of claim 7, wherein no blocking step is required.

10. The method of claim 3, wherein the other strand of said complex of DNA complementary strands is linked to a non-magnetic metallic particle.

* * * * *